United States Patent [19]
Horwitz et al.

[11] Patent Number: 6,054,133
[45] Date of Patent: Apr. 25, 2000

[54] ANTI-MICROBIAL TARGETING FOR INTRACELLULAR PATHOGENS

[75] Inventors: Marcus A. Horwitz; Daniel L. Clemens, both of Los Angeles, Calif.

[73] Assignee: The Regents of the University of California, Oakland, Calif.

[21] Appl. No.: 08/890,858

[22] Filed: Jul. 10, 1997

[51] Int. Cl.$^7$ .......................... A61K 39/08; A61K 45/00; A61K 39/38; A61K 39/395

[52] U.S. Cl. ................................... 424/248.1; 424/278.1; 424/184.1; 424/450; 424/812; 514/2; 514/37; 514/78

[58] Field of Search .............................. 424/248.1, 184.1, 424/450, 278.1, 812; 514/78, 2, 37

[56] References Cited

U.S. PATENT DOCUMENTS

| | | |
|---|---|---|
| 4,193,983 | 3/1980 | Ullman et al. . |
| 4,208,479 | 6/1980 | Zuk et al. . |
| 4,575,484 | 3/1986 | Straus . |
| 5,158,979 | 10/1992 | Clarkson et al. . |
| 5,302,598 | 4/1994 | Clarkson et al. . |
| 5,428,023 | 6/1995 | Russell-Jones et al. . |
| 5,462,969 | 10/1995 | Clarkson et al. . |
| 5,510,264 | 4/1996 | Van Alstyne et al. . |
| 5,543,390 | 8/1996 | Yatvin et al. . |
| 5,543,391 | 8/1996 | Yatvin et al. . |
| 5,612,182 | 3/1997 | Pearson et al. . |
| 5,633,234 | 5/1997 | August et al. . |
| 5,643,599 | 7/1997 | Lee et al. . |
| 5,662,929 | 9/1997 | Lagacé et al. . |
| 5,679,347 | 10/1997 | Porcelli et al. . |
| 5,712,095 | 1/1998 | Britschgi et al. . |
| 5,721,209 | 2/1998 | Horwitz et al. . |
| 5,726,021 | 3/1998 | Britschgi et al. . |
| 5,728,680 | 3/1998 | Morozov et al. . |
| 5,830,478 | 11/1998 | Raso et al. . |
| 5,837,283 | 11/1998 | McDonald et al. . |

FOREIGN PATENT DOCUMENTS

| | | |
|---|---|---|
| 90/01945 | 3/1990 | WIPO . |
| 97/12057 | 4/1997 | WIPO . |

OTHER PUBLICATIONS

Horwitz et al, PNAS, 92:1530–1534, 1995.
Horwitz et al, J. Clin. Invest. 71:15–26, 1983.
Schlesinger et al, Infect & Imm. 62/1:280–289, 1994.
Horwitz, Immunol. Ser. 42(Interferon Nonviral Pathog):287–294, 1988.
Gobin et al J. Exp. Med. 183:1527–1532, Apr. 1996.
Clemens et al, J. Exp. Med. 184:1349–1355, Oct. 1996.
Bhardwaj et al, J. Interferon Res. 8:283–293, 1988.
Armstrong, J.A., D'Arcy Hart, P., "Response of Cultured Macrophages to *Mycobacerium Tuberculosis*, with Observations on Fusion of Lysosomes with Phagosomes," *J. Exper. Med.*, vol. 134, No. 3, pt. 1, (1971), pp. 713–740.
Crowle, A.J., Dahl, R., Ross, E. and May, M.H., "Evidence that Vesicles Containing Living, Virulent *Mycobacterium tuberculosis* of *Mycobacterium avium* in Cultured Human Macrophages are not Acidic," *Infection and Immunity*, vol. 59, No. 5 (1991), pp. 1823–1831.
Songmei, X., Cooper, A., Sturgill–Koszycki, S., van Heyningen, T., Chatterjee, D., Orme, I., Allen, P. and Russell, D.G., "Intracellular Trafficking in *Mycobacterium tuberculosis* and *Mycobacterium avium*–Infected Macrophages," *J. Immunol.*, (1994), pp. 2568–2578.
Clemens, D.L. and Horwitz, M.A., "Characterization of the *Mycobacterium tuberculosis* Phagosome and Evidence that Phagosomal Maturation is Inhibited," *J. Exp. Med.*, vol. 181 (1995) pp. 257–270.
Horwitz, M.A., "The Legionnaires' Disease Bacterium (*Legionella Pneumophila*) Inhibits Phagosome–Lysosome Fusion in Human Monocytes," *J. Exp. Med.*, vol. 158 (1983) pp. 2108–2126.
Horwitz, M.A. and Maxfield, F.R., "*Legionella pneumophila* Inhibits Acidification of its Phagosome in Human Monocytes," *J. Cell Biol.*, vol. 99, (1984), pp. 1936–1943.
Clemens, D.L. and Horwitz, M.A., "Membrane Sorting during Phagocytosis: Selective Exclusion of Major Histocompatibility Complex Molecules but not Complement Receptor CR3 during Conventional and Coiling Phagocytosis," *J. Exp. Med.*, vol. 175 (1992), pp. 1317–1326.
Clemens, D.L. and Horwitz, M.A., "Hypoexpression of Major Histocompatibility Complex Molecules on *Legionella pneumophila* Phagosomes and Phagolysosomes," *Infection and Immunity*, vol. 61, No. 7 (1993), pp. 2803–2812.
Dautry–Varsat, A., Ciechanover, A. and Lodish, H.F., "pH and the recycling of transferrin during receptor–mediated endocytosis," *Proc. Natl. Acad. Sci. USA*, vol. 80 (1983), pp. 2258–2262.
Frens, G., "Controlled Nucleation for the Regulation of the Particle Size in Monodisperse Gold Suspensions," *Nature Phys. Sci.*, vol. 241 (1973), pp. 20–22.
Allison, A.C. and Byars, N.E., "An adjuvant formulation that selectively elicits the formation of antibodies of protective isotypes and of cell–mediated immunity," *J. Immunol. Meth.*, 95 (1986), pp. 157–168.
Rabinowitz, S., Horstmann, H., Gordon, S. and Griffiths, G., "Immunocytochemical Characterization of the Endocytic and Phagolysosomal Compartments in Peritoneal Macrophages," *J. Cell. Biol*, vol. 116, No. 1 (1992), pp. 95–112.

(List continued on next page.)

*Primary Examiner*—Nita Minnifield
*Attorney, Agent, or Firm*—Oppenheimer Wolff & Donnelly LLP

[57] ABSTRACT

A method and composition are provided for treating intracellular pathogens that reside in phagosomes. The compositions include antibiotics which are conjugated with transferrin or other ligands to form conjugates that target membrane-bound pathogens. The conjugates are selectively taken up by infected phagosomes. Conjugates are provided which utilize transferrin as the targeting ligand for treating mycobacterium which reside in membrane-bound phagosomes.

15 Claims, 4 Drawing Sheets

OTHER PUBLICATIONS

Sturgill–Koszycki, S., Schlesinger, P.H., Chakraborty, P., Haddix, P.L., Collins, H.L., Fok, A.K., Allen, R.D., Gluck, S.L., Heuser, J. and Russell, D.G., "Lack of Acidification in Mycobacterium Phagosomes Produced by Exclusion of the Vesicular Proton–ATPase," *Science*, vol. 263 (1994), pp. 678–681.

Harth, G., Lee, B–Y, Wang, J., Clemens, D.L., Horwitz, M.A., "Novel Insights into the Genetics, Biochemistry, and Immunocytochemistry of the 30–Kilodalton Major Extracellular Protein of *Mycobacterium tuberculosis*," *Infection and Immunity*, vol. 64, No. 8 (1996), pp. 3038–3047.

van Renswoude, J., Bridges, K.R., Harford, J.B. and Klausner, R.D., "Receptor–mediated endocytosis of transferrin and the uptake of Fe in K562 cells: Identification of a nonlysosomal acidic compartment," *Proc. Natl. Acad. Sci. USA*, vol. 79 (1982), pp. 6180–6190.

ANTI-MICROBIAL TARGETING FOR INTRACELLULAR PATHOGENS

This invention was made with Government support under Grant No. AI-35275 awarded by the National Institute of Health (NIH). The Government has certain rights in this invention.

BACKGROUND OF THE INVENTION

1. Field of the Invention

The present invention relates generally to the delivery of antibiotics to mammals for use in the treatment of intracellular pathogens. More particularly, the present invention involves the coupling of antibiotics to transferrin to form antibiotic-transferrin conjugates which target pathogens that reside in membrane-bound phagosomes.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography.

*M. tuberculosis* is an intracellular pathogen that parasitizes human mononuclear phagocytes. Throughout its life cycle in these host cells, *M. tuberculosis* resides and multiplies in a membrane-bound phagosome that resists acidification and fusion with lysosomes (1–4). In previous studies, using quantitative immunoelectron microscopy, the composition and maturation of the *M. tuberculosis* phagosome, focusing on known markers of the endocytic pathway have been examined (4). These studies revealed that the *M. tuberculosis* phagosome exhibits delayed clearance of MHC class I molecules, relatively intense staining for MHC class II molecules and the endosomal marker transferrin receptor, and relatively weak staining for the lysosome-associated membrane glycoproteins CD63, LAMP-1, and LAMP-2 and the lysosomal acid protease, cathepsin D. Like *M. tuberculosis*, wild-type *Legionella pneumophila* inhibits phagosome-lysosome fusion and phagosome acidification (5,6). However, in contrast to the *M. tuberculosis* phagosome, the *L. pneumophila* phagosome rapidly clears MHC class I molecules and excludes MHC class II molecules as well as all endosomal-lysosomal markers studied (4,7,8). In contrast to the phagosomes containing either live *M. tuberculosis* or *L. pneumophila*, phagosomes containing heat-killed *M. tuberculosis* or polystyrene beads fuse with lysosomes and stain intensely for lysosome-associated membrane glycoproteins and cathepsin D (4).

There are a number of treatment protocols which are presently being used to treat *M. tuberculosis* and other intracellular pathogens. Many of these protocols involve the use of one or more antibiotic compositions. As in any treatment which utilizes antibiotics, it is desirable to introduce the antibiotic in vivo in such a way as to maximize the effectiveness of the antibiotic against the pathogen. Accordingly, there has been a continuing search to provide new and improved delivery vehicles and systems wherein the efficacy of an antibiotic with respect to a given pathogen is maximized.

SUMMARY OF THE INVENTION

In accordance with the present invention, methods and compositions are provided in which antibiotics are delivered directly and selectively to the pathogen. The invention is based on the discovery that phagosomes which contain pathogens selectively take up transferrin. Delivery of antibiotics directly to the pathogen-containing phagosome is accomplished by conjugating a suitable antibiotic to the transferrin target vehicle. The resulting antibiotic-transferrin conjugate is especially effective against pathogens, such as *M. tuberculosis*, which reside in membrane-bound phagosomes. Other ligands, e.g. LDL (low density lipoprotein), which like transferrin traffic to early endosomes are also suitable for use as delivery vehicles for antibiotics in accordance with the present invention.

The above discussed and many other features and attendant advantages of the present invention will become better understood by reference to the following detailed description when taken in conjunction with the accompanying drawings.

BRIEF DESCRIPTION OF THE DRAWINGS

FIG. 1. Kinetics of delivery of human transferrin to *M. tuberculosis* phagosomes. Human monocyte-derived macrophages were infected with *M. tuberculosis* for three days in culture medium lacking human transferrin, washed with transferrin-free culture medium and incubated with or without human transferrin for 0–60 minutes as indicated. The monocytes were then fixed, prepared for electron microscopy, stained for transferrin by immunogold, and the number of gold particles per phagosome enumerated. A phagosome was considered to stain positive if it contained 2 or more immunogold particles. Results are the mean ± SD for at least 2 grids on which at least 20 cells were counted per grid.

DETAILED DESCRIPTION OF THE INVENTION

The present invention involves the use of transferrin as a targeting vehicle to provide selective delivery of antibiotics to phagosomes which are infected with a pathogen. Transferrin is a serum beta-globulin that transports iron. Transferrin is widely available and can be obtained commercially from a number of sources. For example, transferrin can be obtained from Sigma Chemical Co. (St. Louis, Mo.). Human holo-transferrin is preferred. It is also preferred that multimeric aggregates be removed by centrifuging prior to coupling with antibiotic. Human holotransferrin can also be obtained from Boehringer Mannheim Corporation (Indianapolis, Ind.), Calbiochem (LaJolla, Calif.), or Life Technologies (Gaithersburg, Md.).

In addition, recombinant human transferrin can be expressed by genetic engineering techniques in eukaryotic or prokaryotic cells, purified and loaded with iron. Such recombinant human transferrin can be designed to have other features which will facilitate subsequent coupling of antibiotic drugs to the transferrin. For example, such a recombinant transferrin hybrid molecule can be designed to include an antibody binding moiety or other form of binding moiety capable of binding an antibiotic, or modified antibiotic (e.g. dansylated antibiotic), or the hybrid molecule could be designed to contain a peptide antibiotic.

Transferrin receptors are synthesized in the host cell endoplasmic reticulum (ER) and transported via the golgi to the host cell surface. There, they bind their natural ligand, iron-saturated transferrin, after which the receptor-ligand complexes are internalized in coated vesicles that fuse with early endosomes. Acidification of the early endosome to pH 6.5 to 6.0 causes release of iron from the transferrin. From the endosomal compartment, the apotransferrin-transferrin receptor complexes are rapidly recycled to the plasma membrane (9,10). Transferrin and the transferrin receptor do not traffic through the lysosomal compartment (9,10).

With respect to M. tuberculosis, it is believed that there are three possible sources of the transferrin receptors observed on the phagosome. First, the receptors may be derived by fusion of the phagosome with vesicles coming from the trans-golgi network. Second, the receptors may be derived from the plasma membrane during phagocytosis, and be retained on the phagosome. Third, the receptors may be derived from phagosome interaction with early endosomes. To distinguish the first two from the third possibilities, we administered transferrin exogenously to M. tuberculosis-infected macrophages and examined phagosomes for the presence or absence of transferrin. If transferrin receptors are derived from trans-golgi network or the plasma membrane during phagocytosis, then a pulse of transferrin administered after phagocytosis should not be delivered to the phagosome. On the other hand, if transferrin receptors are derived from phagosome-endosome interaction, exogenously administered transferrin should be delivered to the M. tuberculosis phagosome. In accordance with the present invention, it was found that exogenously administered transferrin is delivered to the M. tuberculosis phagosome, hence demonstrating directly that the M. tuberculosis phagosome interacts with endosomes.

Transferrin is coupled to the antibiotic to form a antibiotic-transferrin conjugate. Antibiotics which may be coupled to transferrin include any of the known antibiotics which are effective in treating a wide variety of diseases in humans and animals including tuberculosis (caused by Mycobacterium tuberculosis, Mycobacterium bovis, and other mycobacteria), leprosy, Mycobacterium avium complex (MAC) infections, Mycobacterium marinum infection, Mycobacterium fortuitum infection, Mycobacterium Kansaii infection, brucellosis, Q fever, tularemia, salmonellosis, typhoid fever, Yersinia infections (including Y. pestis, Y. enterocolitica and Y. pseudotuberculosis), ehrlichiosis, chlamydiosis (including C. psittaci, C. trachomatis), histoplasmosis, toxoplasmosis and leishmaniasis.

Exemplary antibiotics include rifampin, rifabutin, isoniazid, ethambutol, pyrazinamide, thiacetazone, para-aminosalicylic acid, aminoglycosides (including gentamycin, streptomycin, amikacin, kanamycin, viomycin, capreomycin, quinolones (including ciprofloxacin, ofloxacin), ethionamide, prothionamide, cycloserine, dapsone, clofazimine, sparfloxacin, minocycline, clarithromycin, azithromycin, doxycycline, cefoxitin, tetracyclines, cefotaxime, fluoroquinolones, ceftriaxone, chloramphenicol, trimethaprim-sulfamethoxazole, ampicillin, sulfonamides, amoxicillin, ketoconazole, itraconazole, fluconazole, pyrimethamine sulfadiazine, clindamycin, atovaquone sodium stibogluconate, antimonials, amphotericin B, pentamidine, polymixin definsins and other peptide antibiotics used to treat intracellular pathogens. Preferred antibiotics are those which are designed to treat diseases that are caused by intracellular pathogens, especially those that reside within phagosomes during their life cycle in host cells.

The antibiotic is coupled to the native or recombinant transferrins by any of the known coupling mechanisms including antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, and particulate surface adsorption (e.g. colloidal gold).

The resulting antibiotic-transferrin conjugant is delivered to the patient in accordance with any of the conventional drug delivery systems. Exemplary delivery methods include intravenous injection, intramuscular injection, subcutaneous injection, intracutaneous injection, intrathecal injection, intravesicular injection, intraocular injection, intraarticular injection, intraperitoneal injection, intrapleural injection, intraarterial injection, intraumbilical injection, oral ingestion, intranasal administration, inhalation (e.g. aerosol inhalation), intrarectal administration, and subconjunctival administration. The antibiotic-transferrin conjugant is preferably mixed with a pharmaceutically acceptable carrier in accordance with well-known procedures to place the drug in a form which can be administered effectively to the patient. Buffered saline and other similar carriers are preferred.

The amount of antibiotic transferrin conjugant which is administered will vary depending upon the particular conjugant and the disease being treated. The dosage levels can be determined by routine experimentation in accordance with well-known protocols for establishing dosage levels.

The studies described herein demonstrate that endosomes interact with the M. tuberculosis phagosome and, more importantly, deliver ligands bound to endosomal receptors to the *M. tuberculosis* phagosome. In the example described, the receptor is the transferrin receptor and the ligand is transferrin. However, endosomes have other receptors that bind other ligands. For example, endosomes have LDL (low density lipoprotein) receptors that bind LDL. Such ligands also can be delivered to the *M. tuberculosis* phagosome. Hence, as with transferrin, antibiotics can be coupled to LDL or other ligands that target endosomes. The same procedures described herein for coupling antibiotics to transferrin may be used to couple antibiotics to LDL or other ligands that target endosomes. The following examples are directed towards the treatment of *M. tuberculosis*. It will be understood by those skilled in the art that the present invention is not limited to treating this particular pathogen. Instead, the invention has wide application to treating any pathogen which spends at least a part of its lifetime in phagosomes.

MATERIALS AND METHODS

Reagents and Antibodies. Human holo-transferrin was purchased from Sigma Chemical Co. (St. Louis, Mo.). Solutions of transferrin were ultracentrifuged at 150,000×g for 90 minutes at 4° C. to remove multimeric aggregates before incubation with monolayers. Ficoll-hypaque was purchased from Pharmacia (Piscataway, N.J.); glutaraldehyde from Polysciences (Warrington, Pa.); polyvinyl alcohol, polyvinylpyrrolidone, paraformaldehyde from Sigma Chemical Company; RPMI and Dulbecco's PBS from Gibco Laboratories (Santa Clara, Calif.). BSA-colloidal gold and mannan-colloidal gold of homogeneous size distribution (20–25 nm) were prepared by the method of Frens (11).

Mouse monoclonal antibody to human CD63 ($IgG_1$) was purchased from AMAC (Westbrook, Me.); isotypic mouse myeloma control immunoglobulin from Cappel Organon-Technica (Westchester, Pa.); goat-anti-mouse IgG gold conjugates (5 nm) from Sigma Chemical Company; and goat-anti-rabbit IgG gold conjugates (10 nm) from Amersham Corporation (Arlington Heights, Ill.). Rabbit polyclonal antibodies to human transferrin were raised by immunizing rabbits three times, 3 weeks apart, with 1 mg of holo-transferrin in Syntex adjuvant (12). The first immunization was supplemented with 100 $\mu$g of N-acetylmuramyl-L-alanyl-D-isoglutamine. The resulting antibodies had a titer of over 1:10,000 to human transferrin by ELISA and did not cross-react with bovine, goat, or rabbit transferrin or with *M. tuberculosis* antigens.

Bacteria. *M. tuberculosis* Erdman strain (ATCC 35801), a highly virulent strain, obtained from the American Tissue Culture Collection (Rockville, Md.). The organism was passaged through guinea pig lung to maintain virulence, a single-cell suspension obtained, and viability assayed as described previously (4). Viability ranged from 67% to 84% in these experiments.

Preparation of Monocytes and Labeling of Lysosomes. Human mononuclear cells were isolated from fresh heparinized blood of PPD-negative healthy donors using Ficoll-hypaque density gradients. Mononuclear cells ($3\times10^6$/ml) were placed in Falcon 75 $cm^2$ tissue culture flasks (12 ml/flask) in RPMI containing 15% heat-inactivated fetal bovine serum (HI-FBS). Monocytes were allowed to adhere to the plastic for 90 minutes at 37° C. in 5% $CO_2$-95% air, washed three times with RPMI, and incubated in RPMI containing 15% HI-FBS for five days.

In some experiments, monocyte lysosomes were labelled with BSA or mannan conjugated to colloidal gold (BSA-gold or mannan-gold) one day before fixation (13). The BSA-gold or mannan-gold (20–25 nm) was diluted to a final $O.D._{520}$ of 0.5 with RPMI containing 15% HI-FBS. Monocytes were incubated with the gold conjugates for 8 hours at 37° C., washed 4 times with RPMI, and incubated overnight at 37° C. in fresh culture medium.

Infection of monocytes, incubation with transferrin, and localization of antigens by immunogold staining of cryosections. Monocytes in monolayer culture were infected by incubating them with *M. tuberculosis* (0.5–$1\times10^6$/ml) in RPMI containing 15% autologous human serum for 90 minutes at 37° C. As one control, monocytes were incubated with heat-killed (100° C.×10 minutes) *M. tuberculosis* ($2\times10^7$/ml). As a second control, monocytes were co-incubated for 90 minutes at 37° C. with *M. tuberculosis* and polystyrene beads (1 micron spheres, 2% solids, Polysciences) diluted 1:1000. After phagocytosis, monocytes were washed 3 times with RPMI to remove non-adherent bacteria and beads and then incubated for an additional 1–3 days in RPMI containing 15% HI-FBS. Monocyte monolayers were washed 3 times with RPMI and incubated for 15 minutes at 37° C. in serum free RPMI twice (to wash out competing fetal bovine transferrin). Monolayers were then incubated with 1 mg/ml human transferrin in RPMI containing 10% autologous human serum for 0–3 hours at 37° C. The infected monocytes were then fixed with 4% paraformaldehyde, 0.01% glutaraldehyde in 0.15 M sodium cacodylate, pH 7.30 for 2 hours at 4° C.

The fixed monocytes were washed twice with 0.15 M sodium cacodylate, pH 7.3, incubated with 10 mM glycine-HCl in cacodylate buffer for 30 minutes to quench aldehyde groups, and scraped from the culture flasks with Costar cell scrapers into cacodylate buffer containing 0.1% BSA. The monocytes were pelleted by centrifugation at 1000 rpm for 10 minutes, and embedded in 10% gelatin at 37° C. The gelatin was solidified at 0° C. and infiltrated with 2.3 M sucrose, 20% polyvinylpyrrolidone at 4° C. overnight. Cryosections were obtained at −90° C. Sections were transferred to formvar coated nickel grids and incubated with 50% normal goat serum (NGS) and 0.1% fish skin gelatin in 0.9% NaCl in 0.05 M HEPES, pH 7.40 for 1 hour at 4° C. to block nonspecific antibody binding. Sections were incubated with pre-immune serum or rabbit anti-human transferrin diluted 1:500 in HEPES buffer containing 50% NGS and 0.1% fish skin gelatin overnight at 4° C., washed with HEPES buffer, and incubated with goat anti-rabbit Ig conjugated to 10 nm colloidal gold (Sigma) for 90 minutes at room temperature.

For double labeling of sections for CD63, mouse monoclonal antibody (20 $\mu$g/ml) of control isotypic myeloma immunoglobulin were included in the primary antibody incubation, and a 1:9 dilution of goat anti-mouse Ig conjugated to 5 nm colloidal gold (Amersham, Arlington Heights, Ill.) was included in the second antibody incubation step. Sections were washed again with HEPES buffer, postfixed in 2% glutaraldehyde for 5 minutes, washed in distilled water, and embedded in 2% polyvinyl alcohol containing 0.3% uranyl acetate. Sections were viewed with a transmission electron microscope (JEOL, 100 CX II). A latex bead phagosome or *M. tuberculosis* phagosome was considered to stain positively for transferrin if it contained two or more transferrin immunogold particles. In some experiments, photomicrographs of consecutive infected monocytes were made at magnifications of 7,200 to 14,000 and the number of gold particles per micron of membrane were enumerated directly from the negatives using a Numonics 2210 translucent digitizer tablet and Sigma-Scan software program (Jandel Scientific Co., Corte Madera, Calif.).

To demonstrate that exogenously administered transferrin is delivered to the *M. tuberculosis* phagosome, human monocyte-derived macrophages were co-incubated with *M. tuberculosis* and polystyrene beads. The infected macrophages were cultured for three days in RPMI containing heat inactivated-fetal bovine serum. The macrophages were pulsed for inactivated-fetal bovine serum. The macrophages were pulsed for 0–60 minutes with human holo-transferrin (1 mg/ml), fixed, and cryosectioned, and the sections stained specifically for human transferrin using immunogold. In control macrophages, not incubated with human transferrin, only 7% of *M. tuberculosis* phagosomes stained for transferrin (FIG. 1), a level consistent with the background level of staining.

Figure 1:
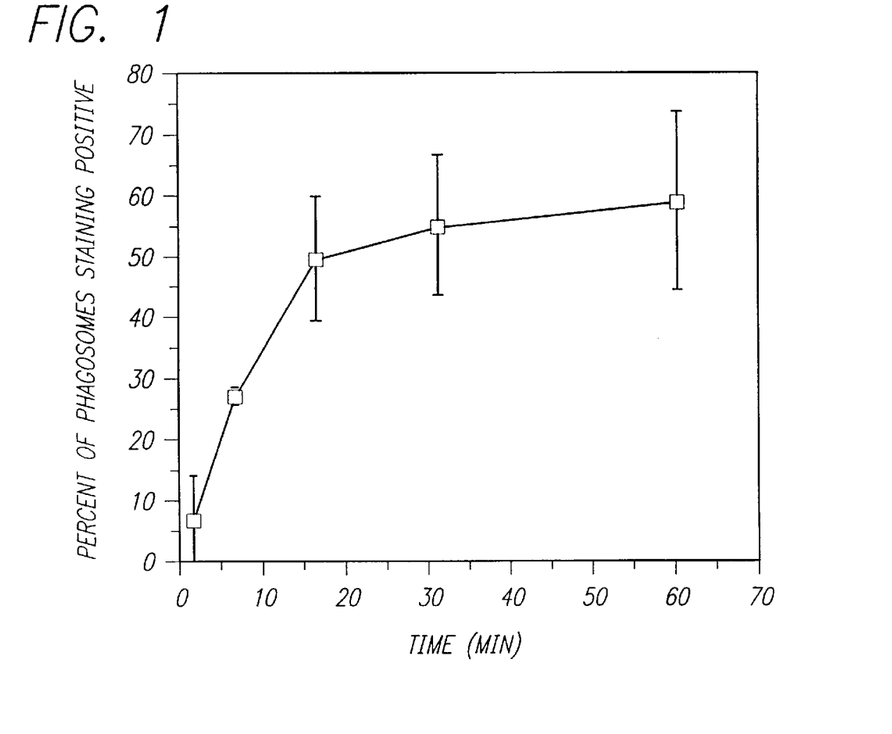
Figure 2:
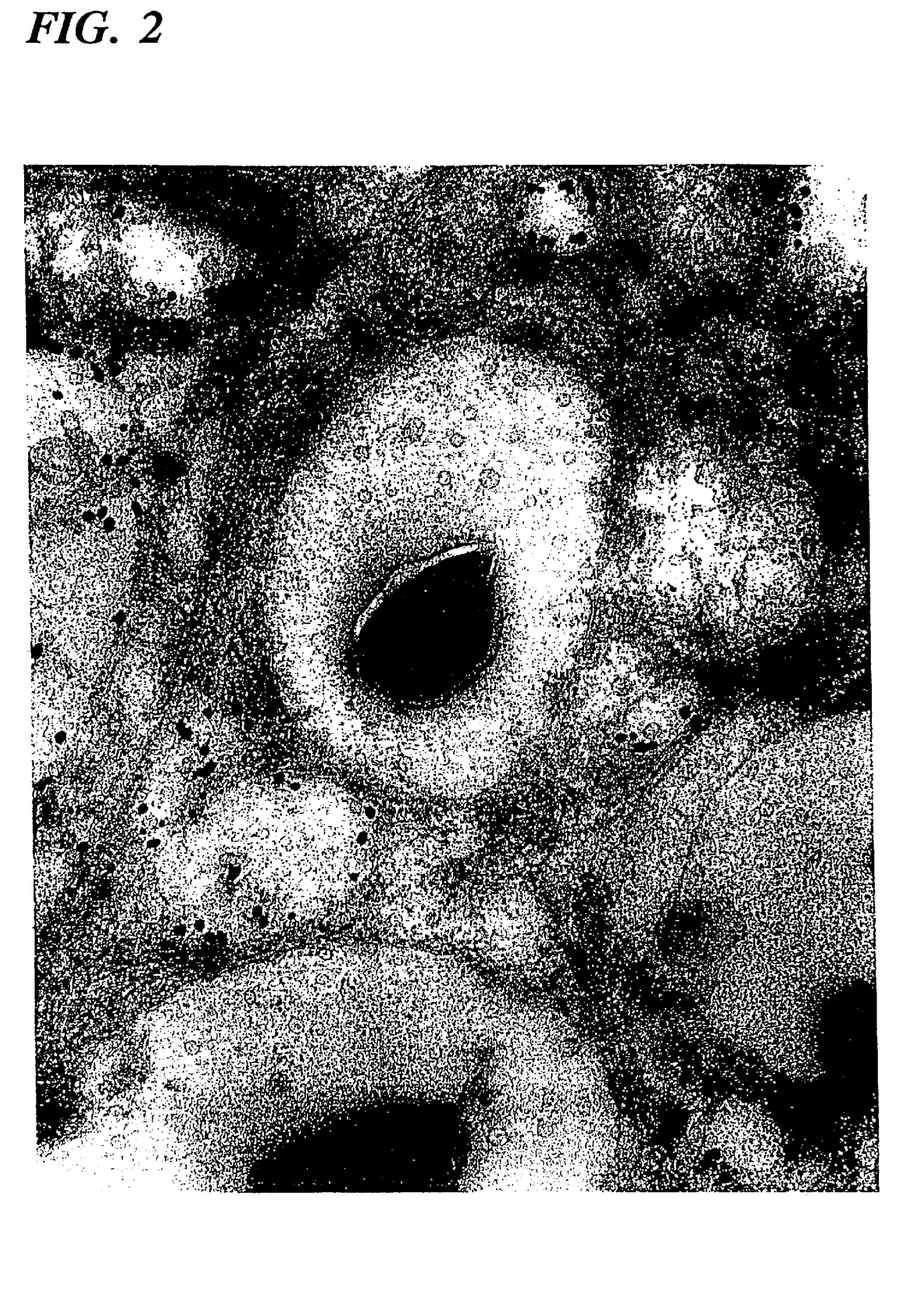
FIG. 2. Cryosection immunogold staining for transferrin in a human monocyte-derived macrophage infected with *M. tuberculosis*. The macrophage was infected with *M. tuberculosis* and pulsed with transferrin for 1 hour as in FIG. 1. Lysosomes in the macrophage were prelabelled by incubating the cells with 20 nm BSA-gold followed by an overnight chase. The *M. tuberculosis* phagosome has acquired abundant transferrin immunogold staining (10 nm gold particles) but has not fused with the BSA-gold labelled compartments. Mag 88,000×.

In macrophages incubated with transferrin, up to 60% of *M. tuberculosis* phagosomes acquired staining for transferrin, depending on the length of incubation (FIGS. 1 and 2). Incorporation of transferrin into the *M. tuberculosis* phagosome was evident at 5 minutes and reached a plateau at 15–30 minutes of incubation, kinetics of labeling consistent with interaction of the *M. tuberculosis* phagosome with early endosomes. Levels of transferrin staining of the *M. tuberculosis* phagosome at 3, 6, and 12 hours were similar to that at 1 hour.

Figure 3A:
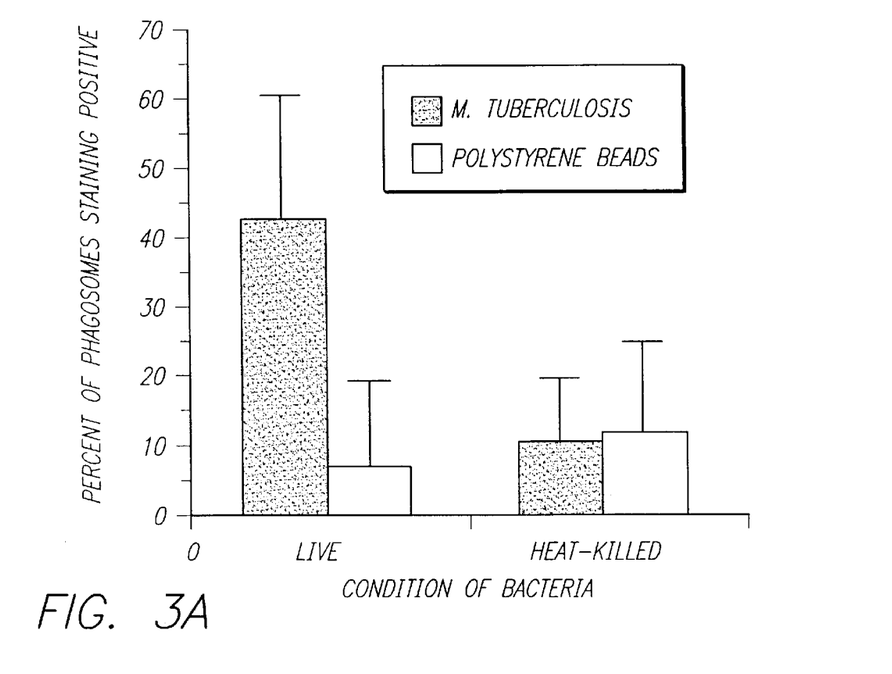
FIG. 3. Delivery of transferrin and mannan-gold to phagosomes containing live or dead *M. tuberculosis* or latex beads. Monocyte-derived macrophages were co-incubated with latex beads and either live or heat-killed *M. tuberculosis*. After 2 days, macrophage secondary lysosomes were labelled by incubation of the cells with mannan-gold for 8 hours. The macrophage monolayers were then washed, and early endosomes were labelled by incubation of the cells with human transferrin for 1 hour. The monolayers were fixed immediately, cryosectioned, and evaluated for transferrin immunogold staining (A) or mannan-gold staining (B) as described in FIG. 1.
Figure 3B:
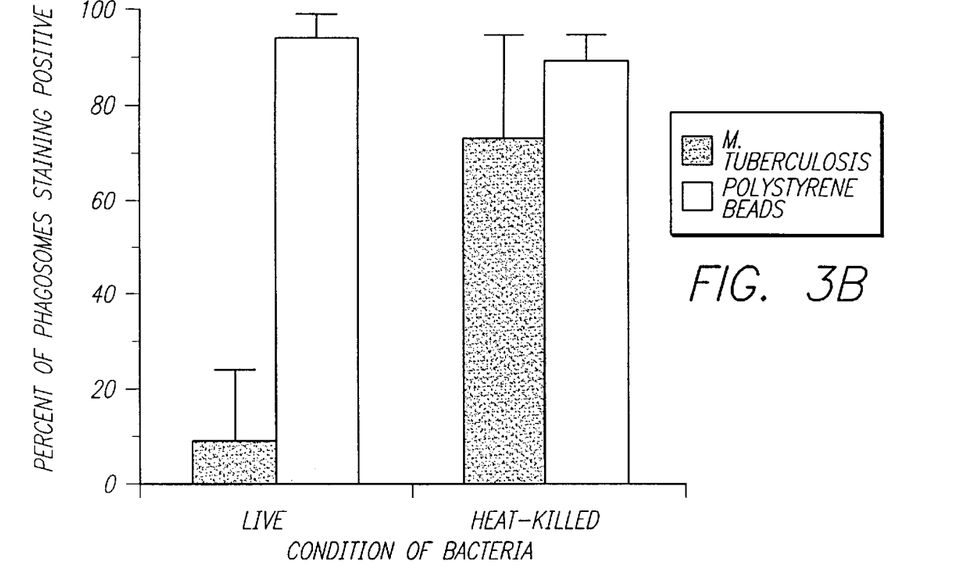

Whereas transferrin was delivered to phagosomes containing live *M. tuberculosis*, transferrin was not delivered to phagosomes containing either polystyrene beads or heat-killed *M. tuberculosis* (FIG. 3A). In contrast, mannan gold particles added to the culture medium after phagocytosis accumulated in phagosomes containing polystyrene beads and heat-killed *M. tuberculosis*, but did not accumulate in phagosomes containing live *M. tuberculosis* (FIG. 3B).

Figure 4:
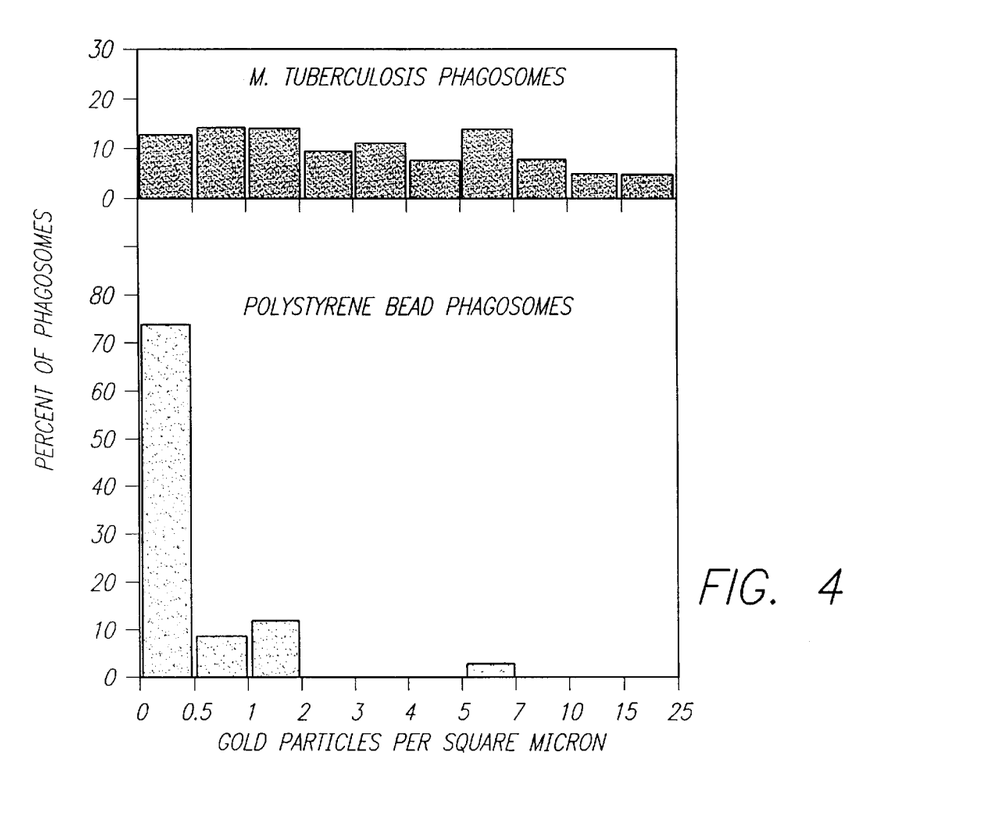
FIG. 4. Distribution of staining for transferrin on phagosomes containing either *M. tuberculosis* or latex beads. Human monocyte-derived macrophages were co-incubated with *M. tuberculosis* and latex beads, and after 3 days, incubated with human transferrin for 3 hours. The macrophages were then fixed, cryosectioned, and stained for transferrin. The number of transferrin immunogold particles per square micron was enumerated for both *M. tuberculosis* phagosomes and polystyrene bead phagosomes.

The *M. tuberculosis* phagosomes which stained positively for transferrin showed a wide distribution in their relative staining intensity (FIG. 4). Moreover, even after infected macrophages were incubated for 12 hours with transferrin, as many as 40% of the *M. tuberculosis* phagosomes did not acquire staining for transferrin. These transferrin-negative phagosomes, however, were not phagolysosomes, since in double labeling experiments, they do not stain for BSA-gold and they are only weakly positive for the lysosomal membrane glycoprotein, CD63.

Figure 5:
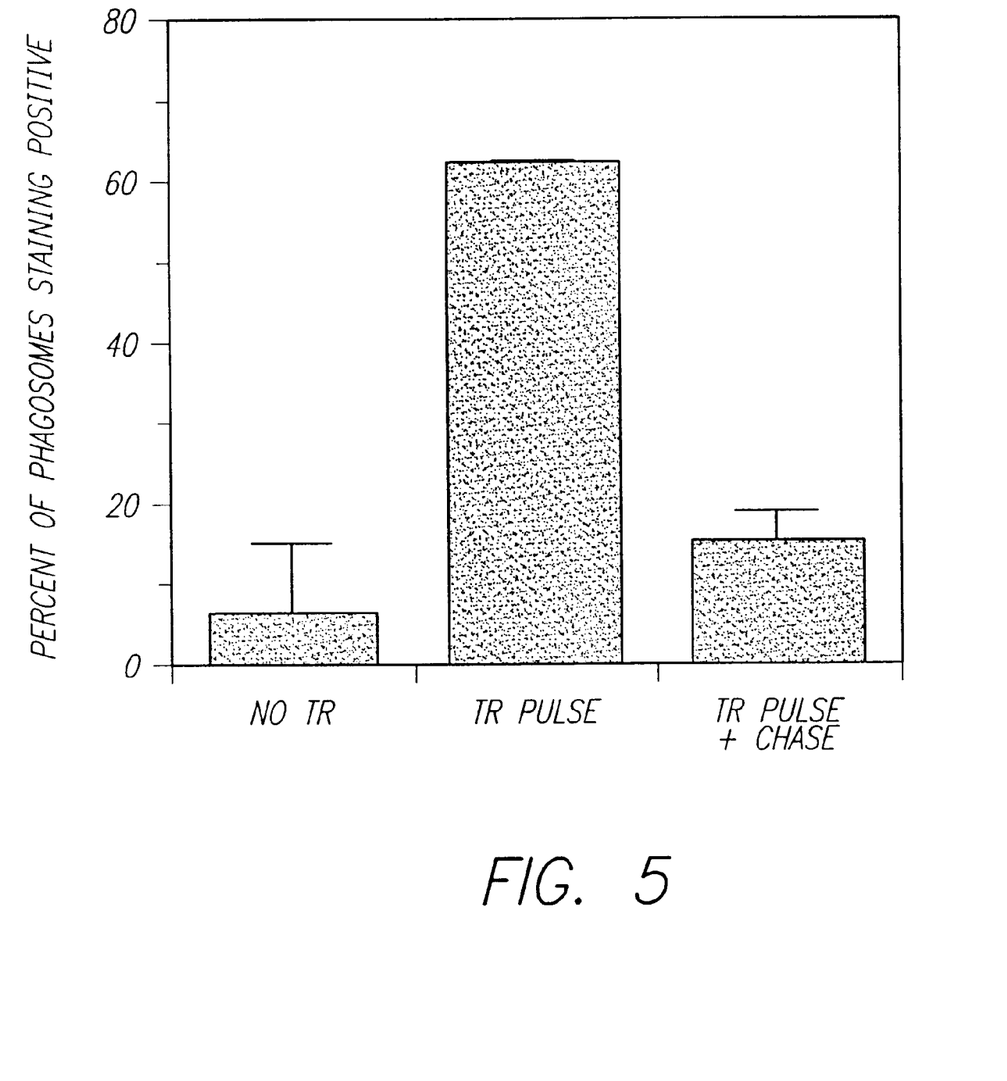
FIG. 5. Transferrin staining of *M. tuberculosis* phagosomes pulsed with human transferrin and chased with transferrin-free medium. Human monocyte-derived macrophages were infected with *M. tuberculosis*, incubated for 3 days, and either fixed (No Tr) or incubated with human transferrin for 1 hour at 37° C. The latter macrophages were either fixed immediately (Tr pulse) or after a 3 hour chase in medium lacking human transferrin (Tr pulse+chase). Samples were sectioned and stained and the percentage of phagosomes staining positive for transferrin enumerated as described above.

In separate experiments, we examined whether human transferrin delivered to the *M. tuberculosis* phagosome could be washed out by a chase with medium lacking human transferrin. We infected human macrophages with *M. tuberculosis*, and 3 days later incubated them with transferrin for 1 hour as described above. We then either fixed the macrophages immediately or fixed them after a 3 hour chase in culture medium lacking human transferrin (containing instead 10% HI-FBS). Whereas 62%±0.5% of *M. tuberculosis* phagosomes in macrophages fixed immediately after incubation with human transferrin stained for transferrin, only 24±12% of *M. tuberculosis* phagosomes fixed after the 3 hour chase stained for transferrin (FIG. 5).

As is apparent from the above examples, exogenously added holo-transferrin does not traffick to late endosomes or lysosomes and serves as a specific marker for early endosomes. The finding that *M. tuberculosis* phagosomes acquire exogenously added transferrin demonstrates that the *M. tuberculosis* phagosomes can exchange material with the early endosomal compartment.

The capacity to interact with early endosomes is a characteristic of early phagosomes as opposed to phagolysosomes. Accordingly, the present invention confirms that *M. tuberculosis* retards the maturation of its phagosome along the endocytic pathway (4). In contrast to phagosomes containing live *M. tuberculosis*, phagosomes containing latex beads and heat-killed *M. tuberculosis* mature to phagolysosomes that do not interact with early endosomes and do not acquire transferrin.

As demonstrated above, the fact that transferrin can be chased out of the *M. tuberculosis* phagosome by medium lacking human transferrin shows that the interaction of the *M. tuberculosis* phagosome with endosomes is bi-directional. In other words, the phagosome can both receive material from and give material to the early endosome. Some evidence suggesting a capacity of the *M. tuberculosis* phagosome to exchange material with the endosomal pathway has also been provided by studies of the distribution of mycobacterial antigens. We have observed the 30/32 kDa major secretory proteins of *M. tuberculosis* in vesicles outside of the *M. tuberculosis* phagosome (15). Xu et al. reported the presence of lipoarabinomannan (LAM) in vesicles outside of the mycobacterial phagosome (3). While these findings are consistent with the idea that the *M. tuberculosis* phagosome interacts with the endosomal pathway in a bi-directional fashion, the possibility remains that mycobacterial antigens reach the endosome-lysosome pathway via an extracellular route.

It should be noted that our discovery that the *M. tuberculosis* phagosome interacts with endosomes is relevant both to the trafficking of mycobacterial antigens within the host cell as well as the targeting of anti-microbials to the *M. tuberculosis* phagosome which is described herein.

We have also found that endosomes interact with *M. tuberculosis* phagosomes from studies of the distribution of Rab5, a protein specific for early endosomes. We have found that Rab5 is rich in *M. tuberculosis* phagosomes, but present at extremely low levels on polystyrene bead phagosomes, which fuse with lysosomes.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

BIBLIOGRAPHY

1. Armstrong, J. A. and P. D. Hart. 1971. Response of cultured macrophages to *M. tuberculosis* with observations on fusion of lysosomes with phagosomes. *J. Exp. Med.* 134:713–740.
2. Crowle, A., R. Dahl, E. Ross, M. May. 1991. Evidence that vesicles containing living virulent *M. tuberculosis* or *M. avium* in cultured human macrophages are not acidic. *Infect. Immun.* 59, 1823–1831.
3. Xu, S., A. Cooper, Sturgill-Koszycki, S. T. van Heynigen, D. Chattedjee, I. Orme, P. Allen, and D. G. Russell. 1994. Intracellular trafficking in *Mycobacterium tuberculosis* and *Mycobacterium avium*-infected macrophages. *J. Immunol.* 153:2568–2578.
4. Clemens, D. L. and M. A. Horwitz. 1995. Characterization of the *Mycobacterium tuberculosis* phagosome and evidence that phagosomal maturation is inhibited. *J. Exp. Med.* 181–257–270.
5. Horwitz, M. A. 1983. The Legionnaires' disease bacterium (*L. pneumophila*) inhibits phagosome-lysosome fusion in human monocytes. *J. Exp. Med.* 158:2108–2126.
6. Horwitz, M. A. and F. R. Maxfield. 1984. *L. pneumophila* inhibits acidification of its phagosomes in human monocytes. *J. Cell. Biol.* 99:1936–1943.
7. Clemens, D. L. and M. A. Horwitz. 1992. Membrane sorting during phagocytosis: Selective exclusion of major histocompatability complex molecules but not complement receptor CR3 during conventional and coiling phagocytosis. *J. Exp. Med.* 175–1317–1326.
8. Clemens, D. L. and M. A. Horwitz. 1993. Hypoexpression of MHC molecules on *L. pneumophila* phagosomes and phagolysosomes. *Infect. Immun.* 61:2803–2812.
9. van Renswoude, J., K. Bridges, J. Harford, and R. Klausner. 1982. Binding of apotransferrin to K562 cells: explanation of the transferrin cycle. *Proc. Natl. Acad. Sci. USA* 79:6186–6190.
10. Dautry-Varsat, A., A. Ciechanover, H. Lodish. 1983. pH and the recycling of transferrin during receptor-mediated endocytosis. *Proc. Natl. Acad. Sci. USA* 80:2258–2262.
11. Frens, G. 1973. Controlled nucleation of the regulation of the particle size in monodisperse gold solutions. *Nature, Phys. Sci.* 241:20–22.
12. Allison, A. C. and N. E. Byars. 1986. Adjuvant formulation for use in vaccines to elicit both cell-mediated and humoral immunity. *J. Immunol. Methods* 95, 157–168.
13. Rabinowitz, S., H. Horstmann, S. Gordon, and G. Griffiths. 1992. Immunocytochemical characterization of the endocytic and phagolysosomal compartments in peritoneal macrophages. *J. Cell Biol* 116:95–112.
14. Sturgill-Koszycki, S., P. Schlesinger, P. Charkroborty, P. Haddix, H. Collins, A. Fok, R. Allen, S. Gluck, J. Heuser, D. Russell. 1994. Lack of acidification in *Mycobacterium phagosomes* produced by exclusion of the vesicular proton-ATPase. *Science* 263:678–681.
15. Harth, G. H., Lee, B.-Y., Clemens, D. L., and Horwitz, M. A. *Genetic, biochemical, and immunocytochemical characterization of the* 30 kDa major extracellular protein of *Mycobacterium. tuberculosis.* Infect. Immun. (In press.)

What is claimed is:

1. A composition for use in delivering an antiboitic to a phagosome which contains a pathogen, said composition comprising an antibiotic coupled to a ligand selected from the group consisting of transferrin and low density lipoprotein.

2. A composition according to claim 1 wherein said ligand is transferrin.

3. A composition according to claim 2 wherein said antibiotic is coupled to transferrin by antigen-antibody interaction.

4. A composition according to claim 2 wherein said antibiotic is coupled to transferrin by an avidin-biotin linkage.

5. A composition according to claim 1 which further comprises a pharmaceutical carrier.

6. A composition according to claim 1 wherein said antibiotic is selected from the group consisting of rifampin, rifabutin, isoniazid, ethambutol, pyrazinamide, thiacetazone, para-aminosalicylic acid, aminoglycosides, quinolones, ethionamide, prothionamide, cycloserine, dapsone, clofazimine, sparfloxacin, minocycline, clarithromycin, azithromycin, doxycycline, cefoxitin, tetracyclines, cefotaxime, fluoroquinolones, ceftriaxone, chloramphenicol, trimethaprim-sulfamethoxazole, ampicillin, sulfonamides, amoxicillin, ketoconazole, itraconazole, fluconazole, pyrimethamine sulfadiazine, clindamycin, atovaquone sodium stibogluconate, antimonials, amphotericin B, pentamidine, polymixin, and defensins.

7. A method for treating a mammal to reduce infection by a pathogen which is located in a phagosome, said method comprising the steps of:

administering to said mammal an antibiotic composition in an amount which is effective to reduce said infection, said antibiotic composition comprising an antibiotic which is coupled to a ligand selected from the group consisting of transferrin and low density lipoprotein.

8. A method for treating a mammal to reduce infection according to claim 7 wherein said antibiotic composition further comprises a pharmaceutical carrier.

9. A method for treating a mammal to reduce infection according to claim 7 wherein said ligand is transferrin.

10. A method for treating a mammal to reduce infection according to claim 9 wherein said antibiotic is coupled to transferrin by antigen-antibody interaction.

11. A method for treating a mammal to reduce infection according to claim 9 wherein said antibiotic is coupled to transferrin by an avidin-biotin linkage.

12. A method for treating a mammal to reduce infection according to claim 7 wherein said antibiotic is selected from the group consisting of rifampin, rifabutin, isoniazid, ethambutol, pyrazinamide, thiacetazone, para-aminosalicylic acid, aminoglycosides, quinolones, ethionamide, prothionamide, cycloserine, dapsone, clofazimine, sparfloxacin, minocycline, clarithromycin, azithromycin, doxycycline, cefoxitin, tetracyclines, cefotaxime, fluoroquinolones, ceftriaxone, chloramphenicol, trimethaprim-sulfamethoxazole, ampicillin, sulfonamides, amoxicillin, ketoconazole, itraconazole, fluconazole, pyrimethamine sulfadiazine, clindamycin, atovaquone sodium stibogluconate, antimonials, amphotericin B, pentamidine, polymixin, and defensins.

13. A method for treating a mammal to reduce infection according to claim 7 wherein said intracellular pathogen is mycobacterium.

14. A method for treating a mammal to reduce infection according to claim 13 wherein said mycobacterium is *M. tuberculosis*.

15. A method for treating a mammal to reduce infection according to claim 7 wherein said antibiotic composition is administered by a method selected from the group consisting of intravenous administration, intramuscular administration and subcutaneous administration.

\* \* \* \* \*